(12) United States Patent
Hölzemann et al.

(10) Patent No.: US 6,326,403 B1
(45) Date of Patent: Dec. 4, 2001

(54) DIACYLHYDRAZINE DERIVATIVES AS INTEGRIN INHIBITORS

(75) Inventors: Günter Hölzemann, Seeheim-Jugenheim; Simon Goodman, Darmstadt; Horst Kessler, Schwalbach; Christoph Gibson, München; Jörg Simon Schmitt, München, all of (DE)

(73) Assignee: Merck Patent Gesellschaft mit, Darmstadt (DE)

( * ) Notice: Subject to any disclaimer, the term of this patent is extended or adjusted under 35 U.S.C. 154(b) by 0 days.

(21) Appl. No.: 09/743,605

(22) PCT Filed: Jul. 6, 1999

(86) PCT No.: PCT/EP99/04673

§ 371 Date: Jan. 12, 2001

§ 102(e) Date: Jan. 12, 2001

(87) PCT Pub. No.: WO00/03973

PCT Pub. Date: Jan. 27, 2000

(30) Foreign Application Priority Data

Jul. 15, 1998 (DE) .............................. 198 31 710

(51) Int. Cl.⁷ .................. C07C 243/38; A01K 31/15
(52) U.S. Cl. ................. 514/563; 546/306; 562/434; 562/560
(58) Field of Search .............. 548/144; 562/560, 562/434; 514/563; 546/306

(56) References Cited

U.S. PATENT DOCUMENTS 5,741,796   4/1998   Hartman et al. ................. 514/300

FOREIGN PATENT DOCUMENTS

92/13552   *   8/1992   (WO) .............................. 548/144

* cited by examiner

*Primary Examiner*—Robert Gerstl
(74) *Attorney, Agent, or Firm*—Millen, White, Zelano & Branigan, P.C.

(57) ABSTRACT

Compounds of the formula I

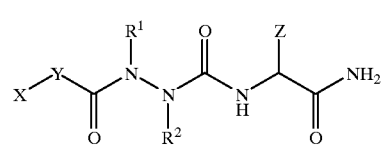

wherein X, Y, Z, $R^1$ and $R^2$ are as defined in claim 1, and their salts and solvates, can be used as integrin inhibitors in particular for the prophylaxis and treatment of circulatory disorders, for thrombosis, cardiac infarction, coronary heart diseases, arteriosclerosis, for pathological processes which are maintained or propagated by angiogenesis and in tumour therapy.

19 Claims, No Drawings

DIACYLHYDRAZINE DERIVATIVES AS INTEGRIN INHIBITORS

This application is a 371 of PCT/EP99/04673 filed Jul. 6, 1999.

The invention relates to compounds of the formula I,

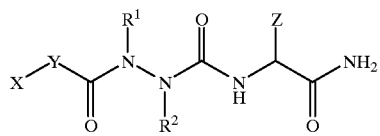

wherein

X is $H_2N\text{—}C(=NH)\text{—}$, $H_2N\text{—}C(=NH)\text{—}NH\text{—}$, $A\text{—}C(=NH)\text{—}NH\text{—}$, $Het^1\text{—}$ or $Het^1\text{—}NH\text{—}$, Y is

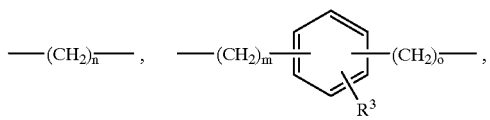

$\text{—}(CH_2)_s\text{—}CH(R^4)\text{—}(CH_2)_t\text{—}$ or $\text{—}(CH_2)_p\text{—}Het^2\text{—}(CH_2)_q\text{—}$, Z is $\text{—}(CH_2)_r\text{—}R^5$, $R^1$, $R^2$ are each independently of one another H or A, $R^3$ is H, F, Cl, Br, A, OA or $OCF_3$, $R^4$ is phenyl which is unsubstituted or substituted by F, Cl, Br, A, OA or $OCF_3$, $R^5$ is COOH, COOA, $CONH_2$, $SO_3H$, $PO_3H_2$ or tetrazolyl, $Het^1$ is a mono- or bicyclic heterocycle having 1 to 4 nitrogen atoms which may be unsubstituted or mono- or disubstituted by $NH_2$, $Het^2$ is a 5- or 6-membered aromatic heterocycle having 1 to 4 nitrogen and/or sulfur atoms which may be unsubstituted or mono- or disubstituted by F, Cl, Br, A, OA or $OCF_3$, A is alkyl having 1 to 6 carbon atoms, n is 0, 1, 2, 3, 4, 5, 6, 7 or 8, m, o, p, q, r, s, t are each independently of one another 0, 1, 2, 3, 4 or 5, and their salts and solvates.

Partially similar compounds are known, for example, from U.S. Pat. No. 5,741,796.

The invention was based on the object of discovering novel compounds having valuable properties, in particular those which can be used for the preparation of medicaments.

It has been found that the compounds of the formula I and their salts have very valuable pharmacological properties, coupled with a good tolerability. Above all, they act as integrin inhibitors, and in particular inhibit the interactions of the $\alpha_v$-, $\beta_3$- or $\beta_5$-integrin receptors with ligands, such as, for example, binding of fibrinogen to the $\beta_3$-integrin receptor. In the case of the integrins $\alpha_v\beta_1$, $\alpha_v\beta_3$, $\alpha_v\beta_5$, $\alpha_{IIb}\beta_3$ and $\alpha_v\beta_6$ and $\alpha_v\beta_8$, the compounds display particular activity; in particular, potent selective inhibitors of the vitronectin receptor $\alpha_v\beta_3$ were found.

This action can be demonstrated, for example, by the method described by J. W. Smith et al. in J. Biol. Chem. 265, 12267–12271 (1990).

The dependence of the development of angiogenesis on the interaction between vascular integrins and extracellular matrix proteins has been described by P. C. Brooks, R. A. Clark and D. A. Cheresh in Science 264, 569–71 (1994).

The possibility of inhibiting this interaction, thus initiating apoptosis (programmed cell death) of angiogenic vascular cells, by a cyclic peptide has been described by P. C. Brooks, A. M. Montgomery, M. Rosenfeld, R. A. Reisfeld, T.-Hu, G. Klier and D. A. Cheresh in Cell 79, 1157–64 (1994).

Compounds of the formula I which block the interaction of integrin receptors and ligands, such as, for example, the binding of fibrinogen to the fibrinogen receptor (glycoprotein IIb/IIIa), prevent, as GPIIb/IIIa antagonists, the spreading of tumour cells by metastasis. This is confirmed by the following observations:

The compounds are capable of inhibiting binding of metalloproteinases to integrins, thus preventing the cells from utilizing the enzymatic activity of the proteinase. An example is found in the inhibition of MMP-2 (matrix metalloproteinase-2) binding to the vitronectin receptor $\alpha_v\beta_3$ by a cyclo-RGD peptide, as described in P. C. Brooks et al., Cell 85, 683–693 (1996).

The spread of tumour cells from a local tumour into the vascular system takes place by the formation of microaggregates (microthrombi) by interaction of the tumour cells with blood platelets. The tumour cells are shielded by the protection in the microaggregate, and are not recognized by the cells of the immune system. The microaggregates can attach themselves to vessel walls, whereby further penetration of tumour cells into tissue is facilitated. Since the formation of the microthrombi is mediated by binding of fibrinogen to the fibrinogen receptors on activated blood platelets, the GPIIa/IIIb antagonists can be regarded as active metastasis inhibitors.

The compounds of the formula I can be employed as medicinally active substances in human and veterinary medicine, in particular for the prophylaxis and/or therapy of thrombosis, myocardial infarction, arteriosclerosis, inflammations, apoplexy, angina pectoris, tumour diseases, osteolytic diseases, such as osteoporosis, pathologically angiogenic diseases, such as, for example, inflammations, opthalmological diseases, diabetic retinopathy, macular degeneration, myopia, ocular histoplasmosis, rheumatic arthritis, osteoarthritis, rubeotic glaucoma, ulcerative colitis, Crohn's disease, atherosclerosis, psoriasis, restenosis after angioplasty, multiple sclerosis, viral infection, bacterial infection, fungal infection, in cases of acute renal failure and in cases of wound healing to assist the healing processes.

The compounds of the formula I can be employed as antimicrobially acting substances during operations where biomaterials, implants, catheters or cardiac pacemakers are used. Here, they have an antiseptic action. The efficacy of the antimicrobial activity can be demonstrated by the method described by P. Valentin-Weigund et al. in Infection and Immunity, 2851–2855 (1988).

Since the compounds of the formula I are inhibitors of fibrinogen binding and thus ligands of the fibrinogen receptors on blood platelets, they can be used as diagnostics for the detection and localization of thrombi in the vascular system in vivo if they are substituted, for example, by a radioactive or UV-detectable radical.

As inhibitors of fibrinogen binding, the compounds of the formula I can also be employed as effective auxiliaries for the study of the metabolism of blood platelets in different activation stages or of intracellular signal mechanisms of the fibrinogen receptor. The detectable unit of a "label" which has to be incorporated, for example isotope labelling by $^3$H, permits the investigation of the abovementioned mechanisms after receptor binding.

The following abbreviations are used below:

Ac acetyl
Asp aspartic acid
Aza-Gly H$_2$N-NH-COOH
BOC tert-butoxycarbonyl
CBZ or Z benzyloxycarbonyl
DCCI dicyclohexylcarbodiimide
DCM dichloromethane
DIPEA diisopropylethylamine
DMF dimethylformamide
EDCI N-ethyl-N,N'-(dimethylaminopropyl)-carbodiimide
Et ethyl
Fmoc 9-fluorenylmethoxycarbonyl
Gly glycine
HATU O-(7-azabenzotriazol-1-yl)-N,N,N',N'-tetramethyluronium hexafluorophosphate
HOBt 1-hydroxybenzotriazole
Me methyl
MBHA 4-methylbenzhydrylamine
Mtr 4-methoxy-2,3,6-trimethylphenylsulfonyl
NMP N-methylpyrrolidone
HONSu N-hydroxysuccinimide
OBzl benzyl ester
OtBu tert-butyl ester
Oct octanoyl
OMe methyl ester
OEt ethyl ester
Pbf 2,2,4,6,7-pentamethyldihydrobenzofuran-5-sulfonyl
POA phenoxyacetyl
Sal salicyloyl
TBTU O-(1H-benzotriazol-1-yl)-N,N,N',N'-tetramethyluronium tetrafluoroborate
TFA trifluoroacetic acid
Trt trityl (triphenylmethyl).

The compounds of the formula I have at least one chiral centre and can therefore be present in a plurality of stereoisomeric forms. All of these forms (for example D and L forms) and their mixtures (for example the DL forms) are embraced by the formula I.

The compounds according to the invention also include so-called prodrug derivatives, i.e. compounds of the formula I which are derivatized with, for example, alkyl or acyl groups, sugars or oligopeptides and which are rapidly cleaved in the organism to the active compounds according to the invention. These also include biodegradable polymer derivatives of the compounds according to the invention, as described, for example, in Int. J. Pharm, 115, 61–67 (1995).

Solvates are addition compounds of the compounds of the formula I with inert solvents. Solvates are, for example, a mono- or dihydrate or an adduct with alcohols, such as, for example, with methanol or ethanol.

The invention furthermore provides a process for preparing compounds of the formula I according to claim 1 and their salts, characterized in that a) a compound of the formula II,

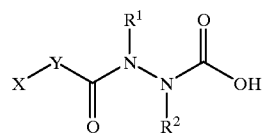

wherein X, Y, R$^1$ and R$^2$ are as defined in claim 1 and wherein free amino groups are protected by a suitable amino protective group, is reacted with a compound of the formula III,

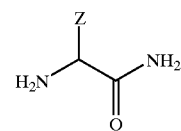

wherein Z is as defined in claim 1, and wherein a free hydroxyl group is protected by a suitable hydroxyl protective group, and the protective groups are subsequently removed, or b) a compound of the formula IV,

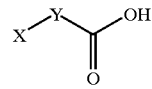

wherein X and Y are as defined in claim 1 and wherein free amino groups are protected by a suitable amino protective group, is reacted with a compound of the formula V,

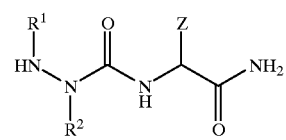

wherein R$^1$, R$^2$ and Z are as defined in claim 1 and wherein a free hydroxyl group is protected by a suitable hydroxyl protective group, and the protective groups are subsequently removed; or c) a compound of the formula I is liberated from one of its functional derivatives by treatment with a solvolysing or hydrogenolysing agent, and/or in that a basic or acidic compound of the formula I is converted into one of its salts by treatment with an acid or base.

In the above formulae, alkyl is preferably methyl, ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl.

Alkylene is preferably methylene, ethylene, propylene, butylene, pentylene or hexylene.

An amino protective group is preferably acetyl, propionyl, butyryl, phenylacetyl, benzoyl, toluyl, POA, methoxycarbonyl, ethoxycarbonyl, 2,2,2-trichloroethoxycarbonyl, BOC, 2-iodoethoxycarbonyl, CBZ ("carbobenzoxy"), 4-methoxybenzyloxycarbonyl, FMOC, Mtr or benzyl.

$R^1$ is preferably H or A, in particular H or Me.

$R^2$ is preferably H, furthermore also methyl.

OA is preferably methoxy, ethoxy, propoxy or butoxy, furthermore also pentyloxy or hexyloxy.

$R^4$ is preferably phenyl which is unsubstituted or mono-substituted by F, Cl, Br, methyl, ethyl, propyl, methoxy, ethoxy or $OCF_3$ and is preferably—as indicated—monosubstituted phenyl, specifically preferably phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-methoxyphenyl, o-, m- or p-ethoxyphenyl, o-, m- or p-fluorophenyl, o-, m- or p-bromophenyl, o-, m- or p-chlorophenyl, o-, m- or p-trifluoromethoxyphenyl.

$R^5$ is preferably COOH, $COOCH_3$, $COOC_2H_5$, COO(t-butyl), $CONH_2$, $PO_3H_2$, $SO_3H$ or tetrazolyl.

$Het^1$ is preferably unsubstituted or mono- or di-$NH_2$-substituted 1-, 2- or 3-pyrrolyl, 1-, 2-, 4- or 5-imidazolyl, 1-, 3-, 4- or 5-pyrazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or -5-yl, 1- or 5-tetrazolyl, 3- or 4-pyridazinyl, pyrazinyl, 1-, 2-, 3-, 4-, 5-, 6- or 7-indolyl, 1-, 2-, 4- or 5-benzimidazolyl, 1-, 3-, 4-, 5-, 6- or 7-benzopyrazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 1H-imidazo[4,5-b]pyridin-2-yl or 1,8-naphthyridin-7-yl. The heterocyclic radicals can also be partially or fully hydrogenated.

$Het^1$ can therefore also be, for example, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4- imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, hexahydro-1-, -3- or -4-pyridazinyl, hexahydro-1-, 2-, -4- or -5-pyrimidinyl, 1-, -2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl or 1,2,3,4-tetrahydro-1,8-naphthyridin-7-yl.

$Het^2$ is preferably unsubstituted or mono-F-, -Cl-, -Br-, -A-, -OA- or -$OCF_3$-substituted 2,3-, 2,4-, 2,5- or 3,4-thienyl, 2,3-, 2,4-, 2,5- or 3,4-pyrrolyl, 2,4-, 2,5- or 4,5-imidazolyl, 2,3-, 2,4-, 2,6- or 3,5-pyridyl, 2,4-, 2,5-, 2,6-, 4,5- or 5,6-pyrimidinyl.

n is preferably 2, 3, 4, 5 or 6, furthermore also 0, 1, 7 or 8; very particularly preferably, n is 3, 4 or 5.

m and o are preferably, in each case independently of one another, 0, 1 or 2, and they are very particularly preferably 0.

s and t are preferably 1 or 2.

p and q are preferably 0 or 1, particularly preferably 0.

Correspondingly, the invention provides in particular those compounds of the formula I in which at least one of the abovementioned radicals has one of the abovementioned preferred meanings. Some preferred groups of compounds can be expressed by the partial formulae Ia to Ii below which correspond to the formula I and where the radicals that are not defined in detail have the meaning given under formula I, but where in Ia) X is $H_2N—C(=NH)—NH—$ in Ib) Y is

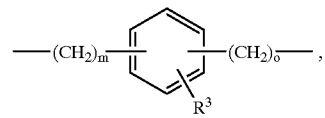

in Ic) Z is —$CH_2$—COOH, in Id) X is $H_2N—C(=NH)—NH—$, $A—C(=NH)—NH—$ or $Het^1—NH—$, in Ie) X is $H_2N—C(=NH)—NH—$ or $Het^1—NH—$, $R^1$ and $R^2$ are H, in If) X is $H_2N—C(=NH)—NH—$ or $Het^1—NH—$, Y is

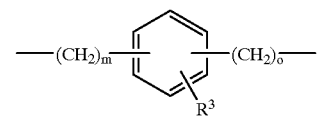

or —$(CH_2)_s$—$CH(R^4)$—$(CH_2)_t$—,

In Ig) X is $H_2N—C(=NH)—NH—$ or $Het^1—NH—$, Y is

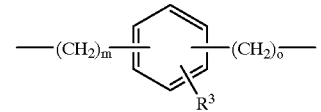

or —$(CH_2)_s$—$CH(R^4)$—$(CH_2)_t$—, z is —$CH_2$—COOH, $R^4$ is unsubstituted or Cl-substituted phenyl, In Ih) X is $H_2N—C(=NH)—NH—$, $A—C(=NH)—NH—$ or $Het^1—NH—$ Y is

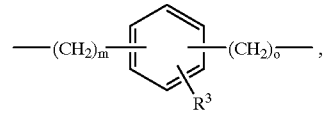

—$(CH_2)_s$—$CH(R^4)$—$(CH_2)_t$ or —$(CH_2)_p$—$Het^2$—$(CH_2)_q$—,

Z is —$CH_2$—COOH, $R^4$ is unsubstituted or Cl-substituted phenyl, $Het^1$ is unsubstituted or mono-$NH_2$-substituted benzimidazolyl, pyridyl, pyrazinyl, pyrimidyl, piperidinyl, piperazinyl, 2,3-dihydroindolyl, indolyl or naphthyridyl, s and t are 1, m,o,p,q are 0 or 1, in Ii) X is $H_2N—C(=NH)—NH—$ or $Het^1—NH—$, Y is

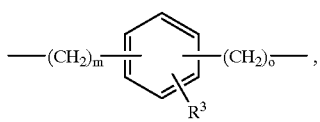

pyridin-2,5-diyl or —(CH$_2$)$_s$—CH (R$^4$)—(CH$_2$)$_t$—,
Z is —CH$_2$—COOH,
R$^4$ is unsubstituted or Cl-substituted phenyl,
Het$^1$ is unsubstituted or mono-NH$_2$-substituted benzimidazolyl, pyridyl, pyrazinyl, pyrimidyl, piperidinyl, piperazinyl, 2,3-dihydroindolyl, indolyl or naphthyridyl,
s and t are 1,
m and o are 0.

The compounds of the formula I and also the starting materials for their preparation are otherwise prepared by methods known per se, such as are described in the literature (for example in the standard works, such as Houben-Weyl, Methoden der organischen Chemie [Methods of Organic Chemistry], Georg-Thieme-Verlag, Stuttgart), and in particular under reaction conditions which are known and suitable for the reactions mentioned. In these reactions, variants which are known per se and are not mentioned here in more detail can also be utilized.

If desired, the starting materials can also be formed in situ, so that they are not isolated from the reaction mixture but are immediately reacted further to give the compounds of the formula I.

Compounds of the formula I can preferably be obtained under the conditions of a peptide synthesis. It is advantageous to employ customary methods of peptide synthesis, as described, for example, in Houben-Weyl, l.c., volume 15/II, pages 1 to 806 (1974).

Thus, compounds of the formula I can be obtained by reacting a compound of the formula II with a compound of the formula III, followed by removal of the protective groups.

It is also possible to obtain the compounds of the formula I by reacting a compound of the formula IV with a compound of the formula V, followed by removal of the protective groups.

The coupling reaction is preferably carried out in the presence of a dehydrating agent, for example a carbodiimide such as DCCI or EDCI, furthermore, for example, propanephosphonic anhydride (cf. Angew. Chem. 92, 129 (1980)), diphenylphosphoryl azide or 2-ethoxy-N-ethoxycarbonyl-1,2-dihydroquinoline, in an inert solvent, for example a halogenated hydrocarbon such as dichloromethane, in an ether such as tetrahydrofuran or dioxane, in an amide such as DMF or dimethylacetamide, a nitrile such as acetonitrile, in dimethyl sulfoxide or in the presence of these solvents, at temperatures between approximately −10 and 40, preferably between 0 and 30°. It is advantageous to work in dilute solutions to promote intramolecular cyclization rather than intermolecular peptide formation. Depending on the conditions employed, the reaction time is between some minutes and 14 days.

Instead of compounds of the formula II and/or IV, it is also possible to employ derivatives of compounds of the formula II and/or IV, preferably a pre-activated carboxylic acid, or a carbonyl halide, a symmetric or mixed anhydride or an activated ester. Such radicals for the activation of the carboxyl group in typical acylation reactions are described in the literature (for example in the standard works such as Houben-Weyl, Methoden der organischen Chemie, Georg-Thieme-Verlag, Stuttgart). Activated esters are advantageously formed in situ, for example by addition of HOBt or N-hydroxysuccinimide.

The reaction is generally carried out in an inert solvent, if a carbonyl halide is used in the presence of an acid binder preferably of an organic base, such as triethylamine, dimethylaniline, pyridine or quinoline.

It may also be favourable to add an alkali metal or alkaline earth metal hydroxide, carbonate or bicarbonate, or another salt of a weak acid of the alkali metals or alkaline earth metals, preferably of potassium, sodium, calcium or caesium.

The direct precursors of the compounds of the formula I can also be synthesized, for example, according to Merrifield (Angew. Chem. 97, 801–812 1985) on a solid phase, a swellable polystyrene resin.

The compounds of the formula I can furthermore be obtained by liberating them from their functional derivatives by solvolysis, in particular hydrolysis, or hydrogenolysis.

Preferred starting materials for the solvolysis or hydrogenolysis are those which otherwise correspond to the formula I but, instead of one or more free amino and/or hydroxyl groups, contain corresponding protected amino and/or hydroxyl groups, preferably those which, instead of an H atom which is bonded to an N atom, carry an amino protective group, in particular those which, instead of an NH$_2$ group, carry an NHR' group (in which R' is an amino protective group, for example BOC or CBZ).

Furthermore, preference is given to starting materials which, instead of the H atom of a hydroxyl group, carry a hydroxyl protective group, for example those which correspond to the formula I but, instead of a hydroxyphenyl group, contain an R"O-phenyl group (in which R" is a hydroxyl protective group).

It is also possible for several—identical or different— protected amino and/or hydroxyl groups to be present in the molecule of the starting material. If the protective groups present differ from one another, in many cases they can be split off selectively.

The term "amino protective group" is generally known and relates to groups which are suitable for protecting (blocking) an amino group from chemical reactions but which can easily be removed after the desired chemical reaction has been carried out at other points of the molecule. Typical such groups are, in particular, unsubstituted or substituted acyl, aryl, aralkoxymethyl or aralkyl groups. Since the amino protective groups are removed after the desired reaction (or reaction sequence), their nature and size is otherwise not critical; however, those having 1–20, in particular 1–8, C atoms are preferred. The term "acyl group" is to be interpreted in the broadest sense in connection with the present process. It includes acyl groups derived from aliphatic, araliphatic, aromatic or heterocyclic carboxylic acids or sulfonic acids, and in particular alkoxycarbonyl, aryloxycarbonyl and, above all, aralkoxycarbonyl groups. Examples of such acyl groups are alkanoyl, such as acetyl, propionyl, butyryl; aralkanoyl, such as phenylacetyl; aroyl, such as benzoyl or toluyl; aryloxyakanoyl, such as POA; alkoxycarbonyl, such as methoxycarbonyl, ethoxycarbonyl, 2,2,2-trichloroethoxycarbonyl, BOC, 2-iodoethoxycarbonyl; aralkyloxycarbonyl, such as CBZ ("carbobenzoxy"), 4-methoxybenzyloxycarbonyl, FMOC; arylsulfonyl, such as Mtr. Preferred amino protective groups are BOC and Mtr, and furthermore CBZ, Fmoc, benzyl and acetyl.

The term "hydroxyl protective group" is also generally known and relates to groups which are suitable for protecting a hydroxyl group from chemical reactions but which can easily be removed after the desired chemical reaction has been carried out at other points of the molecule. Typical such groups are the abovementioned unsubstituted or substituted aryl, aralkyl or acyl groups, and furthermore also alkyl groups. Nature and size of the hydroxyl protective groups is not critical, since they are removed again after the desired chemical reaction or reaction sequence; preference is given to groups having 1–20, in particular 1–10, C atoms. Examples of hydroxyl protective groups are, inter alia, benzyl, p-nitrobenzoyl, p-toluenesulfonyl, tert-butyl and acetyl, benzyl and tert-butyl being particularly preferred. The COOH groups in aspartic acid and glutamic acid are preferably protected in the form of their tert-butyl esters (for example Asp(OBut)).

The liberation of the compounds of the formula I from their functional derivatives is effected—depending on the protective group used—for example with strong acids, expediently with TFA or perchloric acid, but also with other strong inorganic acids, such as hydrochloric acid or sulfuric acid, strong organic carboxylic acids, such as trichloroacetic acid, or sulfonic acids, such as benzene- or p-toluenesulfonic acid. The presence of an additional inert solvent is possible but not always necessary. Suitable inert solvents are, preferably, organic, for example carboxylic acids, such as acetic acid, ethers, such as tetrahydrofuran or dioxane, amides, such as DMF, halogenated hydrocarbons, such as dichloromethane, furthermore also alcohols, such as methanol, ethanol or isopropanol, and also water. Mixtures of the abovementioned solvents are furthermore possible. TFA is preferably used in excess without addition of a further solvent, and perchloric acid is used in the form of a mixture of acetic acid and 70% perchloric acid in a ratio of 9:1. The reaction temperatures for the cleavage are expediently between about 0 and about 50°, and the reaction is preferably carried out at between 15 and 30° (room temperature).

The groups BOC, OBut and Mtr can preferably be cleaved off, for example, with TFA in dichloromethane or with about 3 to 5N HCl in dioxane at 15–30°, and the FMOC group can be cleaved off with an approximately 5 to 50% solution of dimethylamine, diethylamine or piperidine in DMF at 15–30°.

Protective groups which can be removed by hydrogenolysis (for example CBZ or benzyl) can be cleaved off, for example, by treatment with hydrogen in the presence of a catalyst (for example a noble metal catalyst, such as palladium, expediently on a support, such as carbon). Suitable solvents for this reaction are those mentioned above, in particular, for example, alcohols, such as methanol or ethanol, or amides, such as DMF. The hydrogenolysis is generally carried out at temperatures between about 0 and 100° and under pressures between about 1 and 200 bar, preferably at 20–30° and 1–10 bar. Hydrogenolysis of the CBZ group is effected readily, for example, on 5 to 10% Pd/C in methanol, or with ammonium formate (instead of hydrogen) on Pd/C in methanol/DMF, at 20–30°.

A base of the formula I can be converted into the associated acid addition salt using an acid, for example by reaction of equivalent amounts of the base and the acid in an inert solvent, such as ethanol, and subsequent evaporation. Acids which give physiologically acceptable salts are possible, in particular, for this reaction. It is thus possible to use inorganic acids, for example sulfuric acid, nitric acid, hydrohalic acids, such as hydrochloric acid or hydrobromic acid, phosphoric acids, such as orthophosphoric acid, sulfamic acid, or furthermore organic acids, in particular aliphatic, alicyclic, araliphatic, aromatic or heterocyclic mono- or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane or ethanesulfonic acid, ethanedisulfonic acid, 2-hydroxyethanesulfonic acid, benzenesulfonic acid, p-toluenesulfonic acid, naphthalene-mono- and -disulfonic acids and laurylsulfuric acid. Salts with physiologically unacceptable acids, for example picrates, can be used for isolation and/or purification of the compounds of the formula I.

On the other hand, an acid of the formula I can be converted with a base into one of its physiologically acceptable metal or ammonium salts. Salts which are suitable for this purpose are, in particular, the sodium, potassium, magnesium, calcium and ammonium salts, furthermore substituted ammonium salts, for example the dimethyl-, diethyl- or diisopropylammonium salts, monoethanol-, diethanol- or diisopropanolmmonium salts, cyclohexyl-, dicyclohexylammonium salts, dibenzylethylenediammonium salts, furthermore, for example, salts with arginine or lysine.

The invention furthermore provides the use of the compounds of the formula I and/or of their physiologically acceptable salts for the preparation of pharmaceutical formulations, in particular by a non-chemical route. For this purpose, they can be brought into a suitable dosage form together with at least one solid, liquid and/or semi-liquid excipient or auxiliary, and, if appropriate, in combination with one or more further active compounds.

The invention furthermore provides pharmaceutical formulations comprising at least one compound of the formula I and/or one of its physiologically acceptable salts.

These formulations can be used as medicaments in human or veterinary medicine. Possible excipients are organic or inorganic substances which are suitable for enteral (for example oral), parenteral or topical administration or for an administration in the form of an inhalation spray, and which do not react with the novel compounds, for example water, vegetable oils, benzyl alcohols, alkylene glycols, polyethylene glycols, glycerol triacetate, gelatin, carbohydrates, such as lactose or starch, magnesium stearate, talc and vaseline. Tablets, pills, coated tablets, capsules, powders, granules, syrups, juices or drops are used, in particular, for oral administration, suppositories are used for rectal adminstration, solutions, preferably oily or aqueous solutions, and furthermore suspensions, emulsions or implants, are used for parenteral administration, and ointments, creams or powders are used for topical administration. The novel compounds can also be lyophilized and the resulting lyophilisates can be used, for example, for the preparation of injection preparations. The formulations mentioned can be sterilized and/or comprise auxiliaries, such as lubricants, preservatives, stabilizers and/or wetting agents, emulsifiers, salts for influencing the osmotic pressure, buffer substances, dyes, flavourings and/or several other active compounds, for example one or more vitamins.

For administration as an inhalation spray, it is possible to use sprays which contain the active compound either dissolved or suspended in a propellent or propellent mixture (for example $CO_2$ or chlorofluorocarbons). Here, the active compound is expediently employed in micronized form, and one or more additional physiologically acceptable solvents may be present, for example ethanol. Solutions for inhalation can be administered with the aid of customary inhalators.

The compounds of the formula I and their physiologically acceptable salts can be employed as integrin inhibitors for combating diseases, in particular thromboses, cardiac infarction, coronary heart diseases, arteriosclerosis, tumours, osteoporosis, inflammations and infections.

The compounds of the formula I according to claim 1 and/or their physiologically acceptable salts are also used for pathological processes which are maintained or propagated by angiogenesis, in particular for tumours or rheumatoid arthritis.

For this purpose, the substances according to the invention are generally preferably administered in dosages between approximately 0.05 and 500 mg, in particular between 0.5 and 100 mg, per dosage unit, analogously to other known, commercially available peptides, and in particular analogously to the compounds described in U.S. Pat. No. 4,472,305. The daily dosage is preferably between approximately 0.01 and 2 mg/kg of body weight. However, the specific dose for each patient depends on the most diverse factors, for example on the activity of the specific compound employed, on the age, body weight, general state of health, sex, on the diet, on the administration time and route, and on the rate of excretion, medicament combination and severity of the particular disease to which the therapy applies. Parenteral administration is preferred.

The compounds of the formula I can furthermore be employed as integrin ligands for preparing affinity chromatography columns for the preparation of pure integrins.

To this end, the ligand, for example a compound of the formula I, is covalently coupled to a polymer support via an anchor function, for example the carboxyl group of Asp.

Suitable polymeric support materials are the polymeric solid phases which are known per se in peptide chemistry, preferably those having hydrophilic properties, for example crosslinked polysugars, such as cellulose, sepharose or Sephadex®, acrylamides, polyethylene glycol-based polymers or Tentakelpolymere®.

The affinity chromatography materials for the purification of integrin are prepared under conditions like those which are customary for the condensation of amino acids and known per se.

The compounds of the formula I contain one or more chiral centres and may therefore be present in racemic or optically active form. Racemates that are obtained can be separated into the enantiomers by methods which are known per se, mechanically or chemically. Preferably, the racemic mixture is converted into diastereomers by reaction with an optically active resolving agent. Suitable resolving agents are, for example, optically active acids, such as the D and L forms of tartaric acid, diacetyltartaric acid, dibenzoyltartaric acid, mandelic acid, malic acid, lactic acid or the different optically active camphorsulfonic acids, such as β-camphorsulfonic acid. Also advantageous is an enantiomer separation with the aid of a column filled with an optically active resolving agent (for example dinitrobenzoylphenyl-glycine); a suitable mobile phase is, for example, a hexane/isopropanol/acetonitrile mixture, for example in a ratio by volume of 82:15:3.

It is of course also possible to obtain optically active compounds of the formula I by the methods described above by using starting materials which are already optically active.

All temperatures above and below are given in °C. In the following examples, "customary working up" means: water is added, if necessary, the pH is brought to values of between 2 and 10, if necessary, depending on the structure of the end product, the mixture is extracted with ethyl acetate or dichloromethane, the organic phase is separated off, dried over sodium sulfate and evaporated and the residue is purified by silica gel chromatography and/or crystallization. Rf values for silica gel; mobile phase: n-butanol/acetic acid/water 3:1:1 (A), chloroform/methanol 9:1 (B).

RT=retention time (minutes) for HPLC in the following systems:

Column: Nucleosil-5-$C_{18}$ column (250×4; 5 μm).

The eluents used were gradients of acetonitrile (B) with 0.1% TFA and water (A) with 0.1% TFA (data in each case in % by volume of acetonitrile). The retention time $R_t$ was determined at a flow rate of 1 ml/min.

Detection at 220 and 254 nm.

The diastereomers are preferably separated under the given conditions. Mass spectrometry (MS): ESI (electron spray ionization) $(M+H)^+$

EXAMPLE 1

1. 5-(9H-Fluoren-9-ylmethoxy)-3H-[1,3,4]oxadiazol-2-one

Two equivalents of phosgene (1.89 M in toluene; 4.2 ml) are added to a solution of 995 mg of 9H-fluoren-9-yl-methyl hydrazinecarboxylate in 40 ml of dichloromethane and 40 ml of saturated aqueous $NaHCO_3$ solution. The mixture is stirred for 15 minutes and then worked up as usual, giving 5-(9H-fluoren-9-ylmethoxy)-3H-[1,3,4]oxadiazol-2-one ("A").

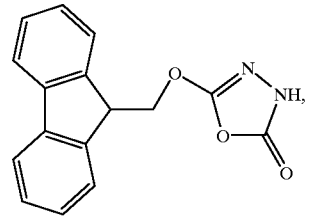

58 mg; IR (KBr): 3300s, 1780s, 1650s, 1451m, 1426m, 1347m, 1224m, 918m, 758w, 740m $cm^{-1}$.

2. Resin-bonded Asp(OtBu)—$NH_2$ ("B")

1.86 g of 4-(4-(1-(9-fluorenylmethoxycarbonyl-amino)ethyl)-2-methoxy-5-nitrophenoxy)butyric acid R-TentaGel resin (0.18 mmol of photolinker/g of resin) were washed in 20 ml of DMF and deprotected twice using 15 ml of 20% piperidine in DMF. After washing with DMF, the resin was admixed with a solution of 0.27 g of Fmoc-Asp(OtBu)-OH, 0.1 g of HOBt and 0.211 g of TBTU in 6 ml of DMF. 0.22 ml of DIPEA is added (up to pH 7), and the mixture is shaken at RT for 1 hour. The mixture is washed with DMF (6×20 ml) and deprotected twice using 15 ml of 20% piperidine in DMF. The mixture is washed with DMF (5×20 ml), methanol (3×20 ml) and diethyl ether (2×20 ml), and the resin is subsequently dried.

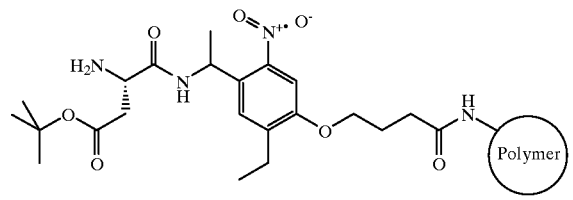

3. Resin-bonded Aza-Gly-Asp(OtBu)—$NH_2$ ("C")

1.12 g of "B" are washed with DCM (3×7 ml), admixed with a solution of 0.176 g of "A" in 5 ml of DCM and shaken for 1 hour.

The mixture is washed with DCM (5×7 ml), NMP (5×7 ml), DMF (3×7 ml) and deprotected twice with 7 ml of 20% piperidine in DMF. The mixture is washed with DMF (5×7 ml), methanol (3×7 ml) and diethyl ether (2×7 ml), and the resin is subsequently dried.

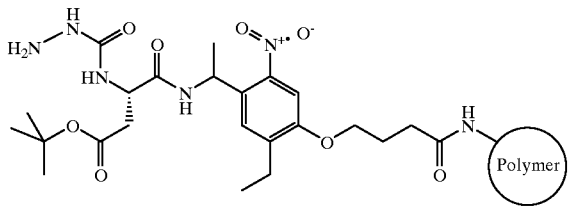

4. (3S)-3-[4-(3-Guanidinobenzoyl)semicarbazido]succinamic acid 0.349 g of "C" is washed with NMP (5×5 ml) and DMF (1×5 ml) and admixed with a solution of 53 mg of 3-(9H-fluoren-9-ylmethoxycarbonylamino)benzoic acid, 56 mg of HATU and 0.24 ml of collidine in 1.5 ml of DMF and the mixture is stirred for 1 hour. The resin is washed and deprotected as described.

The resin is subsequently admixed with a solution of 0.24 g of N,N'-bis-BOC-1-guanylpyrazole ("D") in 2 ml of chloroform and left at 50° for 16 hours. The resin is washed with DCM, methanol and diethyl ether.

To remove the BOC groups, the resin is shaken with a mixture of 95% TFA and 5% $H_2O$ (5 ml) for 1 hour. The resin is washed with DCM, pyridine in DCM, DCM, methanol and diethyl ether. For the cleavage, the resin is suspended in a 1:1 mixture of $ACN/H_2O$ (6 ml) in a plastic syringe, stirred slowly using a magnetic stirrer and irradiated with a TQ 150 mercury immersion lamp for 8 hours. Removal of the solvent and purification by semipreparative HPLC gives (3S)-3-[4-(3-guanidinobenzoyl)semicarbazido]succinic acid, trifluoroacetate.

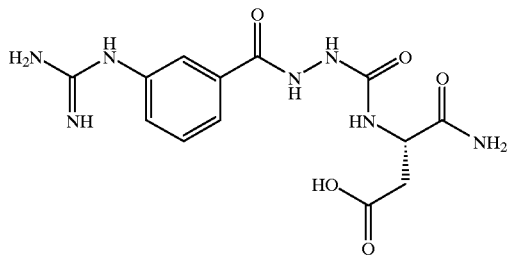

4.8 mg; $R_t$=10.8(0→20, B in A, 30 min) MS (ESI) 352 [M+H]$^+$

EXAMPLE 2

1 molar equivalent of N,N'-bis-BOC-1-guanylpyrozole and 1 molar equivalent of t-butyl (3S)-3-[4-(3-aminobenzoyl)semicarbazido]succinamide [obtainable by reacting 3-(9H-fluoren-9-ylmethoxycarbonylamino)benzoic acid with Aza-Gly-Asp(OtBu)—NH$_2$, followed by removal of the Fmoc group] are stirred in chloroform at 40° for 10 hours. Customary working up gives t-butyl (3S)-3-[4-(3-(N,N'-bis-BOC-guanidyl)benzoyl)semicarbazido]succinamide.

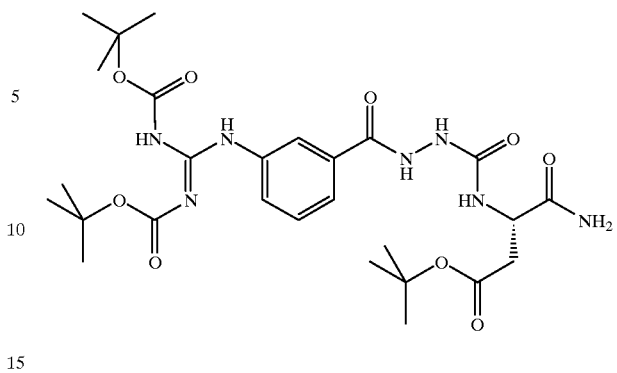

To remove the BOC groups and to cleave the t-butyl ester, the compound is stirred in a mixture of 95% TFA and 5% $H_2O$ for 10 minutes. It is taken up in DCM and worked up as usual, giving (3S)-3-[4-(3-guanidinobenzoyl)semicarbazido]succinamic acid.

EXAMPLE 3

1 molar equivalent of N,N'-bis-BOC-1-guanylbenzoic acid, 1 molar equivalent of Aza-Gly-Asp(OtBu)—NH$_2$ and 1 molar equivalent of HATU are stirred in chloroform at 30° for 10 hours. Customary working up gives t-butyl (3S)-3-[4-(3-(N,N'-bis-BOC-guanidyl)benzoyl)semicarbazido]succinamide.

To remove the BOC groups and to cleave the t-butyl ester, the compound is stirred in a mixture of 95% TFA and 5% $H_2O$ for 10 minutes. The mixture is taken up in DCM and worked up as usual, giving (3S)-3-[4-(3-guanidinobenzoyl)semicarbazido]succinamic acid.

EXAMPLE 4

By the method of Example 1, reaction of 336 mg of "C" with 49 mg of 5-(Fmoc-amino)pentanoic acid, removal of the Fmoc protective group, reaction with 35 mg of "D" and subsequent removal of the Boc protective groups with TFA and cleavage from the resin gives the compound (3S)-3-[4-(5-guanidinopentanoyl)semicarbazido]succinamic acid.

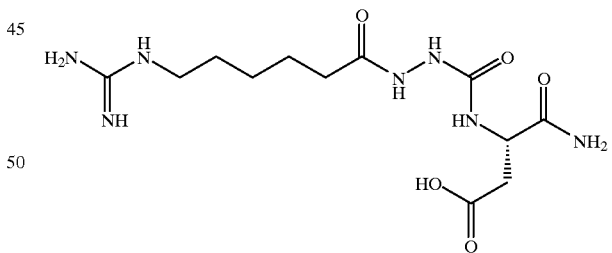

6.0 mg; $R_t$=10.6 (0→30, B in A, 30 min); MS (ESI) 332
Similarly, stepwise reaction of "C"
with 4-(Fmoc-amino)-3-methoxybenzoic acid and "D" and cleavage from the resin gives
(3S)-3-[4-(4-guanidino-3-methoxybenzoyl)semicarbazido]succinamic acid, MS (ESI) 382;
with 2-(Fmoc-amino)pyridine-5-carboxylic acid and "D" and cleavage from the resin gives
(3S)-3-[4-(2-guanidino-pyridine-5-carbonyl)semicarbazido]succinamic acid, MS (ESI) 353.
Similarly, stepwise reaction of resin-bonded Aza-N'-Me-Gly-Asp(OtBu)—NH$_2$ with 5-(Fmoc-amino)pentanoic acid and "D" and cleavage from the resin gives (3S)-3-[4-(5-guanidinopentanoyl)-4-methylsemicarbazido]succinamic acid, MS (ESI) 346;

with 3-(Fmoc-amino)benzoic acid and "D" and cleavage from the resin gives.

(3S)-3-[4-(3-guanidinobenzoyl)-4-methylsemicarbazido]succinamic acid, MS (ESI) 366;

with 3-(Fmoc-amino)phenylacetic acid and "D" and cleavage from the resin gives (3S)-3-[4-(3-guanidinophenylacetyl)-4-methylsemicarbazido]succinamic acid

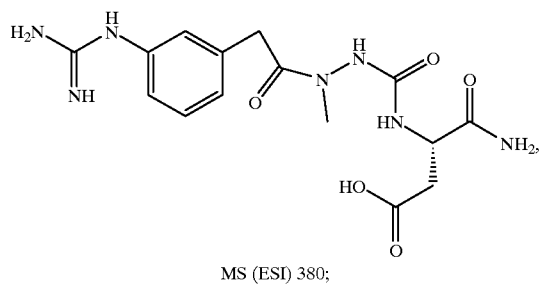

MS (ESI) 380;

with 3-(Fmoc-aminomethyl)benzoic acid and "D" and cleavage from the resin gives (3S)-3-[4-(3-guanidinomethylbenzoyl)-4-methylsemicarbazido]succinamic acid, MS (ESI) 380;

with 4-(Fmoc-amino)benzoic acid and "D" and cleavage from the resin gives (3S)-3-[4-(4-guanidinobenzoyl)-4-methylsemicarbazido]succinamic acid, MS (ESI) 366.

Similarly, stepwise reaction of resin-bonded Aza-N-Me-Gly-Asp(OtBu)—NH$_2$ with 5-(Fmoc-amino)pentanoic acid and "D" and cleavage from the resin gives (3S)-3-[4-(5-guanidinopentanoyl)-3-methylsemicarbazido]succinamic acid, with 3-(Fmoc-amino)benzoic acid and "D" and cleavage from the resin gives (3S)-3-[4-(3-guanidinobenzoyl)-3-methylsemicarbazido]succinamic acid, with 3-(Fmoc-amino)phenylacetic acid and "D" and cleavage from the resin gives (3S)-3-[4-(3-guanidinophenylacetyl)-3-methylsemicarbazido]succinamic acid.

EXAMPLE 5

By the method of Example 1, reaction of "C"

with 4-(1H-benzimidazol-2-ylamino)-3-(4-chlorophenyl)butyric acid gives (3S)-3-{4-[4-(1H-benzimidazol-2-ylamino)-3-(4-chlorophenyl) butanoyl]semicarbazido}succinamic acid

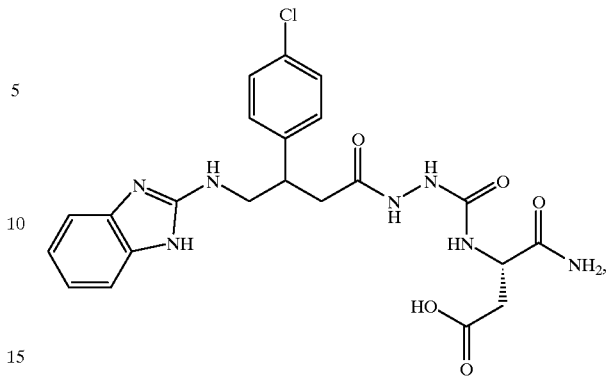

with 4-(2-pyridylamino)-3-(4-chlorophenyl)butyric acid gives (3S)-3-{4-[4-(2-pyridylamino)-3-(4-chlorophenyl)butanoyl]semicarbazido}succinamic acid, with 3-chloro-5-(2-pyridylamino)benzoic acid gives (3S)-3-{4-[3-chloro-5-(2-pyridylamino)benzoyl]semicarbazido}succinamic acid, with 3-(1H-benzimidazol-2-ylamino)benzoic acid gives (3S)-3-{4-[3-(1H-benzimidazol-2-ylamino)benzoyl]semicarbazido}succinamic acid, with 3-acetimidoylbenzoic acid gives (3S)-3-{4-[3-acetimidoylbenzoyl]semicarbazido}-succinamic acid,

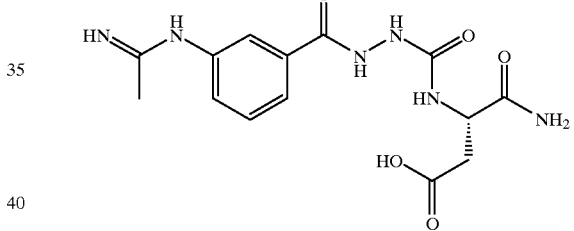

The following examples relate to pharmaceutical formulations:

Example A

Injection Vials

A solution of 100 g of an active compound of the formula I and 5 g of disodium hydrogen phosphate in 3 l of doubly distilled water is brought to pH 6.5 with 2 N hydrochloric acid and subjected to sterile filtration, and injection vials are filled with the solution, lyophilized under sterile conditions and closed under sterile conditions. Each injection vial contains 5 mg of active compound.

Example B

Suppositories

A mixture of 20 g of an active compound of the formula I with 100 g of soya lecithin and 1400 g of cocoa butter is melted, poured into moulds and allowed to cool. Each suppository contains 20 mg of active compound.

Example C

Solution

A solution is prepared from 1 g of an active compound of the formula I, 9.38 g of NaH$_2$PO$_4$.2H$_2$O, 28.48 g of Na$_2$HPO$_4$.12H$_2$O and 0.1 g of benzalkonium chloride in 940 ml of doubly distilled water. It is brought to pH 6.8, topped up to 1 l and sterilized by irradiation. This solution can be used in the form of eye drops.

Example D

Ointment 500 mg of an active compound of the formula I are mixed with 99.5 g of vaseline under aseptic conditions.

Example E

Tablets

A mixture of 1 kg of active compound of the formula I, 4 kg of lactose, 1.2 kg of potato starch, 0.2 kg of talc and 0.1 kg of magnesium stearate is pressed to tablets in the customary manner such that each tablet contains 10 mg of active compound.

Example F

Coated tablets

Tablets are pressed analogously to Example E and are then coated in the customary manner with a coating of sucrose, potato starch, talc, tragacanth and dyestuff.

Example G

Capsules

Hard gelatin capsules are filled with 2 kg of active compound of the formula I in the customary manner such that each capsule contains 20 mg of the active compound.

Example H

Ampoules

A solution of 1 kg of active compound of the formula I in 60 l of doubly distilled water is subjected to sterile filtration, and ampoules are filled with the solution, lyophilized under sterile conditions and closed under sterile conditions. Each ampoule contains 10 mg of active compound.

Example I

Inhalation spray 14 g of the active compound of the formula I are dissolved in 10 l of isotonic NaCl solution, and the solution is filled into customary commercial spray containers having a pump mechanism. The solution can be sprayed into mouth or nose. One squirt (approximately 0.1 ml) corresponds to a dose of approximately 0.14 mg.

What is claimed:

1. Compounds of the formula I,

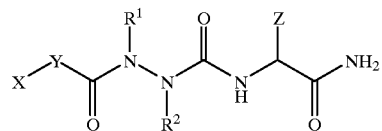

I wherein

X is $H_2N-C(=NH)-$, $H_2N-C(=NH)-NH-$, $A-C(=NH)-NH-$, $Het^1-$ or $Het^1-NH-$,

Y is

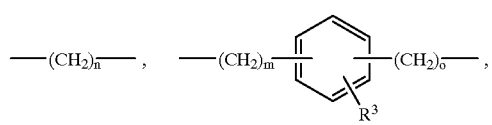

$-(CH_2)_s-CH(R^4)-(CH_2)_t-$ or $-(CH_2)_p-Het^2-(CH_2)_q-$,

Z is $-(CH_2)_r-R^5$, $R^1$, $R^2$ are each independently of one another H or A, $R^3$ is H, F, Cl, Br, A, OA or $OCF_3$, $R^4$ is phenyl which is unsubstituted or substituted by F, Cl, Br, A, OA or $OCF_3$, $R^5$ is COOH, COOA, $CONH_2$, $SO_3H$, $PO_3H_2$ or tetrazolyl, $Het^1$ is a mono- or bicyclic heterocycle having 1 to 4 nitrogen atoms which may be unsubstituted or mono- or disubstituted by $NH_2$, $Het^2$ is a 5- or 6-membered aromatic heterocycle having 1 to 4 nitrogen and/or sulfur atoms which may be unsubstituted or mono- or disubstituted by F, Cl, Br, A, OA or $OCF_3$, A is alkyl having 1 to 6 carbon atoms, n is 0, 1, 2, 3, 4, 5, 6, 7 or 8, m, o, p, q, r, s, t are each independently of one another 0, 1, 2, 3, 4 or 5, and their salts and solvates.

2. A compound according to claim 1 a) (3S)-3-[4-(3-guanidinobenzoyl)semicarbazido] succinamic acid or a physiologically acceptable salt thereof;

b) (3S)-3-[4-(5-guanidinopentanoyl)semicarbizido] succinamic acid or a physiologically acceptable salt thereof;

c) (3S)-3-[4-(4-guanidino-3-methoxybenzoyl) semicarbazido]succinamic acid or a physiologically acceptable salt thereof;

d) (3S)-3-[4-(2-guanidino-pyridine-5-carbonyl) semicarbazido]succinimaic acid or a physiologically acceptable salt thereof;

e) (3S)-3-[4-(5-guanidinopentanoyl)-4-methylsemicarbazido]succinamic acid or a physiologically acceptable salt thereof;

f) (3S)-3-[4-(3-guanidinophenylacetyl)-4-methylsemicarbazido]succinamic acid or a physiologically acceptable salt thereof;

g) (3S)-3-[4-(3-guanidinomethylbenzoyl)-4-methylsemicarbazido]succinamic acid or a physiologically acceptable salt thereof;

h) (3S)-3-[4-(4-guanidinobenzoyl)-4-methylsemicarbazido]succinamic acid or a physiologically acceptable salt thereof;

i) (3S)-3-[4-(5-guanidinopentanoyl)-3-methylsemicarbazido]succinamic acid or a physiologically acceptable salt thereof;

j) (3S)-3-[4-(3-guanidinobenzoyl)-3-methylsemicarbazido]succinamic acid or a physiologically acceptable salt thereof;

k) (3S)-3-[4-(3-quanidophenylacetyl]-3-methylsemicarbazido]succinamic acid or a physiologically acceptable salt thereof.

3. A process for preparing a compound according to claim 1, comprising:

a) reacting a compound of the formula II, $$\underset{\underset{O}{\overset{R^1}{X-Y-C-N-N-C-OH}}}{\overset{O}{\|}}\quad II$$

wherein X, Y, R¹ and R² are as defined in claim 1 and wherein free amino groups are protected by a suitable amino protective group,
with a compound of the formula III, $$H_2N-\underset{\underset{O}{\overset{Z}{|}}}{CH}-C-NH_2 \quad III$$

wherein Z is as defined in claim 1, and wherein a free hydroxyl group is protected by a suitable hydroxyl protective group, and the protective groups are subsequently removed; or
b) reacting a compound of the formula IV, $$X-Y-C-OH \quad IV$$

wherein X and Y are as defined in claim 1 and wherein free amino groups are protected by a suitable amino protective group, with a compound of formula V, $$V$$

wherein R¹, R², and Z are as defined in claim 1 and wherein a free hydroxyl group is protected by a suitable hydroxyl protective group, and the protective groups are subsequently removed; or
c) liberating a compound of the formula I from a starting material which contains protected amino and/or hydroxyl groups by treating with a solvolysing or hydrogenolysing agent; and/or
d) converting a basic or acidic compound of the formula I into one of its salts by treating with an acid or base.

4. Process for the preparation of pharmaceutical formulations, characterized in that a compound of the formula I according to claim 1 and/or one of its physiologically acceptable salts is/are brought into a suitable dosage form together with at least one solid, liquid or semi-liquid excipient or auxiliary.

5. Pharmaceutical formulation, characterized in that it comprises at least one compound of the formula I according to claim 1 and/or one or its physiologically acceptable salts.

6. A method for treating thrombosis, cardiac infarction, coronary heart disease, arteriosclerosis, tumors, osteoporosis, inflammation, and/or infection comprising administering to a patient a therapeutically effective amount of a compound according to claim 1.

7. A method for treating a pathological process which is maintained or propagated by angiogenesis comprising administering to a patient with said pathological process a therapeutically effective amount of a compound according to claim 1.

8. A method for preparing a medicament for treating thrombosis, cardiac infarction, coronary heart disease, arteriosclerosis, tumors, osteoporosis, inflammation, and/or infection comprising formulating a compound of formula I and/or its physiologically acceptable salts according to claim 1 in said medicament.

9. A method for treating a disease involving an integrin receptor comprising administering to a patient with said disease a therapeutically effective amount of an integrin inhibitor compound according to claim 1.

10. A compound according to claim 1, wherein X is $H_2N-C(=NH)-NH-$.

11. A compound according to claim 1, wherein Y is $$-(CH_2)_m-\underset{R^3}{\bigcirc}-(CH_2)_o-.$$

12. A compound according to claim 1, wherein Z is $-CH_2-COOH$.

13. A compound according to claim 1, wherein X is $H_2N-C(=NH)-NH-$, $A-C(=NH)-NH-$ or $Het^1-NH-$.

14. A compound according to claim 1, wherein X is $H_2N-C(=NH)-NH-$ or $Het^1-NH-$, and R¹ and R² are each H.

15. A compound according to claim 1, wherein X is $H_2N-C(=NH)-NH-$ or $Het^1-NH-$,
Y is $$-(CH_2)_m-\underset{R^3}{\bigcirc}-(CH_2)_o-$$

or $-(CH_2)_s-CH(R^4)-(CH_2)_t-$.

16. A compound according to claim 1, wherein X is $H_2N-C(=NH)-NH-$ or $Het^1-NH-$,
Y is $$-(CH_2)_m-\underset{R^3}{\bigcirc}-(CH_2)_o-$$

or $-(CH_2)_s-CH(R^4)-(CH_2)_t-$,
Z is $-CH_2-COOH$, and
R⁴ is unsubstituted or Cl-substituted phenyl.

17. A compound according to claim 1, wherein X is $H_2N-C(=NH)-NH-$, $A-C(=NH)-NH-$ or $Het^1-NH-$ Y is

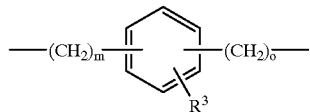

—(CH$_2$)$_s$—CH(R$^4$)—(CH$_2$)$_t$ or —(CH$_2$)$_p$—Het$^2$—(CH$_s$)$_q$—,

Z is —CH$_2$—COOH,

R$^4$ is unsubstituted or Cl-substituted phenyl,

Het$^1$ is unsubstituted or mono-NH$_2$-substituted benzimidazolyl, pyridyl, pyrazinyl, pyrimidyl, piperidinyl, piperazinyl, 2,3-dihydroindolyl, indolyl or naphthyridyl, s and t are 1, and m, o, p, q are 0 or 1.

18. A compound according to claim 1, wherein X is H$_2$N—C(=NH)—NH— or Het$^1$—NH—, Y is

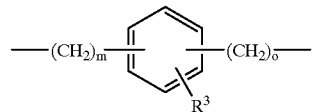

pyridin-2,5-diyl or —(CH$_2$)$_s$—CH(R$^4$)—(CH$_2$)$_t$—,

Z is —CH$_2$—COOH,

R$^4$ is unsubstitued or Cl-substituted phenyl,

Het$^1$ is unsubstituted or mono-NH$_2$-substituted benzimidazolyl, pyridyl, pyrazinyl, pyrimidyl, piperidinyl, piperazinyl, 2,3-dihydroindolyl, indolyl or naphthyridyl, s and t are 1, and m and o are 0.

19. A pharmaceutical composition comprising a compound according to claim 1, and at least one solid, liquid or semi-solid excipient or auxilliary.

* * * * *